United States Patent

Szántay et al.

[11] Patent Number: 4,746,665
[45] Date of Patent: May 24, 1988

[54] NITRO DERIVATIVES OF VINBLASTINE-TYPE BISINDOLES, AND PHARMACEUTICAL COMPOSITIONS CONTAINING THEM

[75] Inventors: Csaba Szántay; Lajos Szabó; Katalin Honty; Tibor Keve; Tibor Ács; Sándor Eckhardt; János Sugár; Zsuzsa Somfai; Evá Iván; Zsuzsa Kneffel, all of Budapest, Hungary

[73] Assignee: Richter Gedeon Vegyeszeti Gyar, Budapest, Hungary

[21] Appl. No.: 873,537

[22] Filed: Jun. 12, 1986

[30] Foreign Application Priority Data

Jun. 12, 1985 [HU] Hungary .................. 2302/85

[51] Int. Cl.⁴ .................. A61K 31/475; C07D 519/04
[52] U.S. Cl. .................................. 514/283; 540/478
[58] Field of Search .................. 540/478; 514/283

[56] References Cited

U.S. PATENT DOCUMENTS

| 4,029,663 | 6/1977 | Gutowski et al. | 540/478 |
| 4,322,350 | 3/1982 | Langlois et al. | 540/478 |
| 4,419,359 | 12/1983 | Keve et al. | 514/283 |

FOREIGN PATENT DOCUMENTS

| 0174459 | 3/1986 | European Pat. Off. | 546/51 |
| 2342980 | 9/1977 | France | 514/283 |
| 2094787 | 9/1982 | United Kingdom | 546/51 |

Primary Examiner—Donald G. Daus
Assistant Examiner—Diana G. Rivers
Attorney, Agent, or Firm—Keil & Weinkauf

[57] ABSTRACT

The invention relates to novel nitro derivatives of the general formula (I)

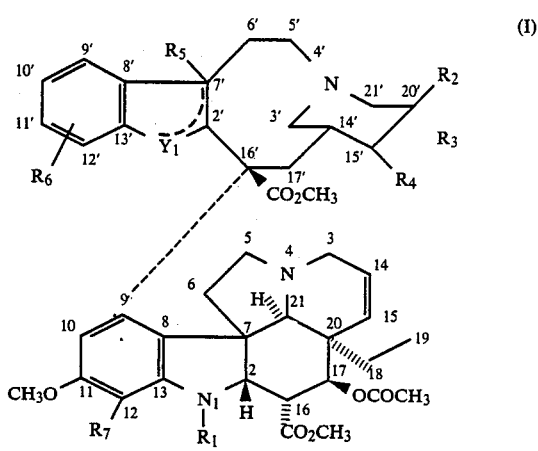

wherein
$R_1$ stands for a methyl or a formyl group;
$R_2$ stands for a hydroxy or ethyl group of $\beta$-position;
$R_3$ means an ethyl group of $\alpha$-position;
$R_4$ represents a hydrogen atom; or
$R_3$ and $R_4$ together represent an oxygen bridge or a double bond;
$R_5$, $R_6$ and $R_7$ stand for a nitro group or hydrogen atom, with the proviso that simultaneously only one of them may stand for hydrogen atom; and
Y stands for —N= when $R_5$ stands for a nitro group; whereas
Y stands for —NH— when $R_5$ stands for a hydrogen atom and a valence bond exists between the $C_2$, and $C_7$, atoms, as well as their acid addition salts and pharmaceutical preparations containing these compounds.

Further on, the invention relates to a process for preparing these compounds and preparations.

The compounds of the general formula (I) show a cytostatic activity with less toxicity than that of the known vinblastine-type bis-indole alkaloid drugs which are commercially available.

3 Claims, No Drawings

NITRO DERIVATIVES OF VINBLASTINE-TYPE BISINDOLES, AND PHARMACEUTICAL COMPOSITIONS CONTAINING THEM

The invention relates to novel nitro derivatives of vinblastine-type bisindoles of the general formula (I),

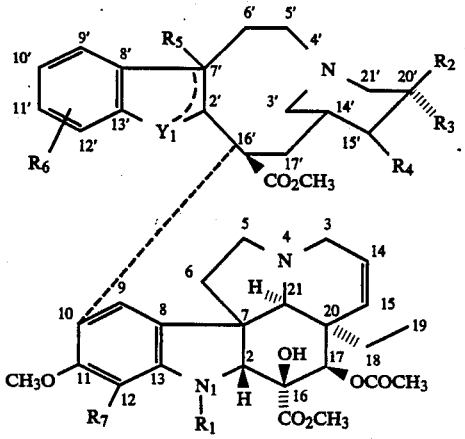

wherein
$R_1$ stands for a methyl or a formyl group;
$R_2$ stands for a hydroxy or ethyl group of $\beta$-position;
$R_3$ means an ethyl group of $\alpha$-position;
$R_4$ represents a hydrogen atom; or
$R_3$ and $R_4$ together represent an oxygen bridge or a double bond;
$R_5$, $R_6$ and $R_7$ stand for a nitro group or hydrogen atom, with the proviso that simultaneously only one of them may stand for hydrogen atom; and
Y stands for —N= when $R_5$ stands for a nitro group; whereas
Y stands for —NH— when $R_5$ stands for a hydrogen atom and a valence bond exists between the $C_2$ and $C_7$ atoms,
as well as their acid addition salts and pharmaceutical preparations containing these compounds.

According to an other aspect of the invention, there is provided a process for the preparation of the new compounds of the general formula (I) and their acid addtion salts.

It is known from the literature that relatively few compounds have hitherto been described in which the aromatic nucleus of the bis-indole alkaloid derivative was substituted. Among these compounds, the 15',20'-anhydro-7'-chloro-vinblastine [Chem. Abstr. 94, 309887k (1981)], the 10'-hydroxyleurosine [J. Nat. Prod. 44, 478 (1981)] as well as the 10'-iodovinblastine (U.S. Pat. No. 4,430,269) are remarkable.

No literature data, however, are available on nitro-bis-indole derivatives substituted on their aromatic nucleus.

Now it has been found in the course of our investigations that various mononitro derivatives are formed in excellent yields when the known bis-indole alkaloids are nitrated by using fuming nitric acid in a solvent mixture consisting of glacial acetic acid and chloroform.

Based on these fact, there is provided a process for preparing the compounds of the general formula (I), wherein $R_1$, $R_2$, $R_3$, $R_4$, $R_5$, $R_6$, $R_7$ and Y are the same as defined above, and their acid addition salts, which comprises (a) reacting a compound of the general formula (II),

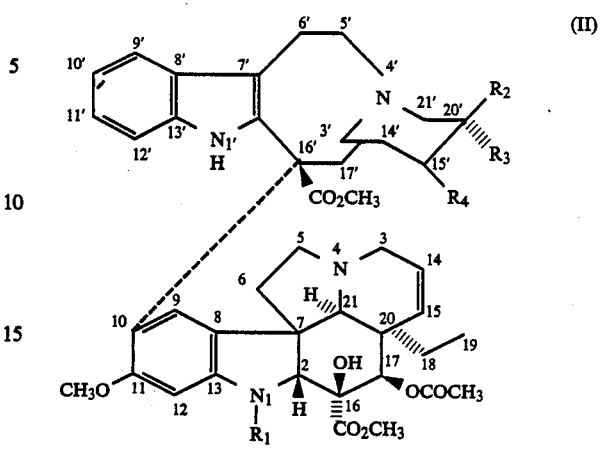

wherein $R_1$, $R_2$, $R_3$ and $R_4$ are the same as defined above, in an organic solvent, preferably in a chlorinated hydrocarbon, in the presence of an organic acid, preferably in the presence of acetic acid, or (b) dehydratating a compound of the general formula (I), wherein $R_1$, $R_2$, $R_5$, $R_6$ and $R_7$ are the same as defined above, $R_3$ means an ethyl group of $\alpha$-position and $R_4$ represents hydrogen atom, and oxidizing the thus-obtained compound, whereby the meaning of $R_3$ and $R_4$ together is changed to an oxygen bridge, and, if desired, transforming the thus-obtained product to an acid addition salt thereof.

The compounds of the general formula (I) show a cytostatic effect with less toxicity than that of the known vinblastine-type bis-indole alkaloid drugs which are commercially available.

For investigating the biological activity, the solutions were prepared by using physiological saline and, if desired, in the case of bases, by adding one drop of Tween-80. The injectable solutions were intraperitoneally administered in a volume of 0.1 ml/10 g of body-weight.

The activity of the novel compounds of the invention was investigated on intraperitoneally transplantable tumours (P388 mouse leukaemia) by using the method described hereinafter.

The P388 leukaemia was maintained in DBA2 inbred mice and transplanted intraperitoneally by administering $10^6$ tumour cells/animal to groups consisting of 6 BDF$_1$ hybride mice each. In the 24th hour following the transplantation, the treatment with the compounds to be tested was started with daily intraperitoneal injections for 8 days. The body-weight, condition and tumour of the animals were daily controlled. The effect was measured on lengthening of the life span in days and expressed as the percentage of the mean suvival time of the treated group as related to that of the control group (T/C %).

It is obvious from Table 1 that the compounds of the invention advantageously influence the life span of the mice suffering from P388 leukaemia. It can be seen that the broadness of the action of 11'-nitrovincristine is preferred. A single daily dose of 8 to 16 mg/kg of body weight and even a high single dose of 20 to 40 mg/kg of body weight was tolerated by the animals without any paralysis or mortality, respectively, oppositely to vincristine which is only effective when used in repeated doses.

TABLE 1

| Compound | Dose mg/kg i.p. | Mean survival time Treated days | Mean survival time Control days | T/C % |
|---|---|---|---|---|
| 12-Nitrovinblastine | 8 × 4.0 | 11.4 | 9.0 | 127 |
|  | 8 × 8.0 | 15.4 | 9.6 | 160 |
|  | 8 × 16.0 | 15.6 | 9.6 | 163 |
| 7'-Nitrovincristine | 8 × 2.0 | 11.0 | 9.6 | 115 |
|  | 8 × 8.0 | 16.8 | 9.6 | 175 |
|  | 1 × 20.0 | 16.0 | 9.6 | 167 |
| 11'-Nitrovincristine | 8 × 0.4 | 12.0 | 9.8 | 122 |
|  | 8 × 1.0 | 14.0 | 9.8 | 147 |
|  | 8 × 2.0 | 16.8 | 9.8 | 171 |
|  | 8 × 8.0 | 20.8 | 9.6 | 217 |
|  | 8 × 12.0 | 19.0 | 9.2 | 198 |
|  | 1 × 20.0 | 15.2 | 9.2 | 158 |
|  | 1 × 40.0 | 18.0 | 9.2 | 196 |
| 11'-Nitrovincristine sulphate | 8 × 1.0 | 14.4 | 10.0 | 144 |
|  | 8 × 4.0 | 18.2 | 10.0 | 182 |
|  | 8 × 8.0 | 16.0 | 9.2 | 174 |
| Vincristine (a known substance) | 8 × 0.05 | 11.1 | 9.0 | 123 |
|  | 8 × 0.1 | 18.7 | 9.2 | 203 |
|  | 8 × 0.2 | 16.8 | 9.2 | 186 |
|  | 8 × 0.4 | 21.7 | 9.2 | 236 |

On carrying out the process (a) of the invention, the starting material of the general formula (II) is dissolved in a solvent, preferably in a mixture of chloroform with glacial acetic acid. Fuming nitric acid is added to this solution at a temperature of about $-20°$ C. ($-20\pm2°$ C.), then the reaction mixture is poured into ice-water. After alkalization and extraction, the crude product is purified by layer or column chromatography.

On carrying out the process (b) of the invention, a compound of the general formula (I) is chosen which contains a nitro group bound to the aromatic nucleus and can be transformed by a simple chemical operation, e.g. by dehydratation or oxidation.

After accomplishing the above reactions, the product is obtained from the reaction mixture by extraction and/or evaporation and, if desired, purified by using a chromatographical and/or crystallization method. The chromatography is carried out on a sheet or column prepared with silica gel.

The starting materials used in process (a) of the invention are known compounds.

The starting materials used in process (b) of the invention are new compounds which are prepared according to the process (a).

The invention is illustrated in detail by the aid of the following non-limiting Examples.

EXAMPLE 1

Preparation of 12-nitrovinblastine by the nitration of vinblastine

A solution containing 0.09 ml (0.136 g, 2.16 mmoles, 3.3 equivalents) of fuming nitric acid (d=1.5) in 0.38 ml of glacial acetic acid is dropped to a solution containing 0.53 g (0.65 mmole) of vinblastine in a solvent mixture of 1.25 ml of glacial acetic acid and 1 ml of abs. chloroform within 10 minutes under constant stirring and maintaining the temperature at $-20°$ C. Then the reaction mixture is poured into 10 ml of ice-water, alkalized to pH 9 by adding concentrated ammonium hydroxide solution and extracted 3 times with 5 ml of dichloromethane each. After drying over anhydrous magnesium sulphate, the organic solution is filtered and evaporated to give 0.50 g of an oily product which is purified by preparative thin layer chromatography (TLC) on a KG-PF$_{254+366}$ sheet by using a developing system containing dichloromethane and methanol in a ratio of 20:2.

The R$_f$ value of vinblastine is lower than that of the nitro derivative which is in turn lower than that of the oxidized product. The elution is carried out with a 20:4 mixture containing dichloromethane and methanol. The aimed compound is obtained in a yield of 2.75 mg (49%); m.p.: decomposition beginning from 200° C.; $[\alpha]_{546}^{21} = -234°$; $[\alpha]_D^{21} = -212°$ (c=1.00, chloroform). IR (KBr, cm$^{-1}$): 3460 (NH, OH), 1735 (ester CO), 1520, 1375 (NO$_2$).

MS m/z (%): 869 (M+14, with an intensity changing with time), 855 (M$^+$, 3, C$_{46}$H$_{57}$N$_5$O$_{11}$), 825 (5), 824 (8), 696 (1), 367 (10), 355 (8), 294 (5), 155 (50), 154 (67), 122 (52), 121 (75), 107 (60), 106 (100).

$^1$H-NMR (CDCl$_3$):δ=8.02 (indole NH), 7.52–7.10 (4H, m, 9'-, 10'-, 11'-, 12'-H), 6.82 (1H, s 9-H), 5.87 (1H, dd, 14-H), 5.45 (1H, s, 17-H), 5.35 (1H, d, 15-H), 3.87 (1H, s, 2-H), 3.77, 3.72, 3.66 (9H, s, CO$_2$CH$_3$, OCH$_3$), 2.82 (2H, 21'-H), 2.63 (3H, s, NCH$_3$), 2.16 (3H, s, OCOCH$_3$), 0.88 (3H, t, 18-CH$_2$CH$_3$), 0.76 ppm (3H, t, 18'-CH$_2$CH$_3$).

EXAMPLE 2

Preparation of 11'-nitrovincristine, 9'-nitrovincristine and 7'-nitrovincristine by the nitration of vincristine A solution containing 0.15 ml (0.228 g, 3.6 mmoles, 3.5 equivalents) of fuming nitric acid (d=1.5) in 0.65 ml of glacial acetic acid is dropped to a solution containing 0.85 g (1.03 mmoles) of vincristine in a mixture of 2.65 ml of abs. chloroform and 2.10 ml of glacial acetic acid at $-20°$ C., whereupon the stirring is continued at the same temperature for additional 3 hours. Then the mixture, is poured into 60 ml of ice-water, alkalized to pH 9 by adding concentrated ammonium hydroxide solution and extracted 3 times with 20 ml of dichloromethane each. After drying over anhydrous magnesium sulphate, filtering and evaporating, the thus-obtained product wheighing 0.89 g is separated by using preparative TLC on a KG-PF$_{254+366}$ sheet by means of a developing system containing dichloromethane and methanol in a ratio of 20:2. The elution is carried out with a 20:4 mixture of dichloromethane and methanol. The order of the R$_f$ values is as follows: 7'-nitrovincristine>9'-nitrovincristine>11'-nitrovincristine>vincristine. By using the above method, the 11'-, 9'- and 7'-nitro derivatives can be separated.

11'-Nitrovincristine is obtained in a yield of 0.54 g (60%); m.p.: 225° C. (with decomposition); $[\alpha]_D^{21} = +92°$; $[\alpha]_{546}^{21} = +112°$ C. (c=1.00, chloroform).

IR (KBr, cm$^{-1}$): 3360 (NH, OH), 1725 (ester CO), 1660 (NCHO). MS m/z (%): 883 (M+14, 0.4), 869 (M$^+$, 1.0, C$_{46}$H$_{55}$N$_5$O$_{12}$), 852 (0.6), 838 (2.1), 393 (1.3), 355 (1.0), 302 (5.5), 205 (3.8), 154 (40), 141 (20), 136 (12), 122 (16), 120 (6.9), 106 (14), 74 (79), 72 (92).

$^1$H-NMR (CDCl$_3$): δ=8.7, 8.56 (1H, NCHO), 8.60 (1H, s, indole NH), 8.13 (1H, J$_m$=2 Hz, 12'-H), 7.97 (1H, J$_o$=9 Hz, J$_m$=2 Hz, 10'-H), 7.54 (1H, J$_o$=9 Hz, 9'-H), 6.76 (1H, s, 9-H), 5.92 (1H, dd, 14-H), 5.42 (1H, d, 15-H), 5.22 (1H, s, 17-H), 4.62 (1H, s, 2-H), 3.86, 3.72, 3.68 (9H, s, CO$_2$CH$_3$, OCH$_3$), 2.04 (3H, s, OCOCH$_3$), 0.88 (3H, t, 18-CH$_2$CH$_3$), 0.76 (3H, t, 18'-CH$_2$CH$_3$).

From the middle zone, 9'-nitrovincristine is isolated in a yield of 50 mg (5%); m.p.: 220° C. (with decomposition); $[\alpha]_{546}^{27} = +109.5°$ (c=1.00, chloroform). IR (KBr, cm$^{-1}$): 3480 (NH, OH), 1730 (ester CO), 1680 (NCHO).

MS m/z (%): 883 (M+14, 0.05), 869 (M+, 1.0, $C_{46}H_{55}N_5O_{12}$).

$^1$H-NMR (CDCl$_3$): δ=8.62 (1H, s, indole NH), 8.52 (1H, br, NHCO), 7.45 (1H, $J_o$=8 Hz, $J_m$=1.5 Hz, 10'-H), 7.35 (1H, $J_o$=8.5 Hz, $J_m$=1.5 Hz, 12'-H), 7.13 (1H, dd, $J_o$=8, 8.5 Hz, $J_m$=1.5 Hz, 11'-H), 5.90 (1H, dd, 14-H), 5.42 (1H, d, 15-H), 5.22 (1H, s, 17-H), 4.63 (1H, s, 2-H), 3.85, 3.73, 3.67 (9H, s, CO$_2$CH$_3$, OCH$_3$), 2.02 (3H, s, OCOCH$_3$), 0.84 (3H, t, 18-CH$_2$C$\underline{H}_3$), 0.65 ppm (3H, t, 18'-CH$_2$C$\underline{H}_3$).

Finally, 7'-nitrovincristine is obtained in a yield of 0.28 g (31%) from the zone characterized by the highest R$_f$ value, m.p.: 212° C. (with decomposition) after recrystallization from methanol; $[α]_D^{20}$=−95°; $[α]_{546}^{20}$=−112° (c=1.00, chloroform). IR (KBr, cm$^{-1}$): 3420 (OH), 1735 (ester CO), 1678 (NCHO), 1552 (C=N).

MS m/z (%): 869 (M+, 1.0, $C_{46}H_{55}N_5O_{12}$), 838 (6.4), 393 (8.4), 391 (3.7), 355 (12), 205 (17), 182 (21), 154 (87), 141 (37), 136 (36), 122 (51), 121 (88), 120 (28).

$^1$H-NMR (CDCl$_3$): δ=8.46 (1H, NCHO), 7.70 (1H, s, 12-H), 7.46–6.90 (5H, m, aromatic protons), 5.92 (1H, dd, 14-H), 5.42 (1H, d, 15-H), 5.22 (1H, s, 17-H), 4.70 (1H, s, 2-H), 3.75, 3.42 (9H, s, CO$_2$CH$_3$, OCH$_3$), 2.00 (3H, s, OCOCH$_3$), 0.88 (3H, t, 18-CH$_2$C$\underline{H}_3$), 0.79 (3H, t, 18'-CH$_2$CH$_3$).

EXAMPLE 3

Preparation of N-formyl-11'-nitroleurosine and N-formyl-7'-nitroleurosine by the nitration of N-formylleurosine A solution containing 0.16 ml (0.24 g, 3.85 mmoles) of fuming nitric acid in 0.68 ml of glacial acetic acid is dropped to a solution containing 0.89 g (1.08 mmoles) of N-formylleurosine base in the solvent mixture of 2.19 ml of glacial acetic acid and 14 ml of abs. chloroform at −20° C., then the stirring is continued at the same temperature for additional 3 hours, whereupon the reaction mixture is poured into 10 ml of ice-water, alkalized to pH 9 by adding concentrated ammonium hydroxide solution and extracted 3 times with 30 ml of dichloromethane each. After drying over anhydrous magnesium sulphate, filtering and evaporating, the thus-obtained oily product weighing 0.68 g is separated by using preparative TLC on KG-PF$_{254+366}$ sheet by means of a developing system containing dichloromethane and methanol in a ratio of 20:2. The R$_f$ value of N-formyl-11'-nitroleurosine is higher than that of the starting N-formylleurosine. The elution is carried out with a 20:4 mixture of dichloromethane and methanol.

N-Formyl-11'-nitroleurosine is obtained in a yield of 0.23 g (24.5%); m.p.: 215° C. (with decomposition), after rubbing with ether; $[α]_D^{21}$=+105°; $[α]_{546}^{21}$=+136° (c=1.00, chloroform).

IR (KBr, cm$^{-1}$): 3400 (OH), 1730 (ester CO), 1660 (NCHO).

$^1$H-NMR (CDCl$_3$): δ=8.72 (1H, s, indole-NH), 8.13 (1H, $J_m$=2 Hz, 12'-H), 7.96 (1H, $J_o$=9 Hz, $J_m$=2 Hz, 10'-H), 7.54 (1H, $J_o$=9 Hz, 9'-H), 7.2–6.9 (1H, 12-H), 6.79 (1H, s, 9-H), 5.96 (1H, dd, 14-H), 5.46 (1H, d, 15-H), 5.22 (1H, s, 17-H), 4.65 (1H, s, 2-H), 3.88, 3.73, 3.68, (9H, s, CO$_2$CH$_3$, OCH$_3$), 2.06 (3H, s, OCOCH$_3$), 0.95 (3H, t, 18-CH$_2$C$\underline{H}_3$), 0.74 ppm (3H, t, 18'-CH$_2$CH$_3$).

From the zone characterized by the higher R$_f$ value, N-formyl-7'-nitroleurosine can be obtained in a yield of 70 mg (7%); m.p.: 219° C. (with decomposition) after rubbing with ether; $[α]_D^{21}$=−77°; $[α]_{546}^{21}$=−83° (c=1.00, chloroform).

$^1$H-NMR (CDCl$_3$): δ=8.54 (1H, br, NCHO), 7.90 (1H, s, 12-H), 7.50–7.18 (5H, m, aromatic protons), 5.85 (1H, dd, 14-H), 5.27 (1H, d, 15-H), 5.12 (1H, s, 17-H), 4.68 (1H, s, 2-H), 3.76, 3.74, 3.68 (9H, s, CO$_2$CH$_3$, OCH$_3$), 1.94 (3H, s, OCOCH$_3$), 0.92 (3H, t, 18-CH$_2$C$\underline{H}_3$), −0.12 ppm (3H, t, 18'-CH$_2$C$\underline{H}_3$).

EXAMPLE 4

Preparation of 15',20'-anhydro-11'-nitrovincristine

Method (a)

A solution containing 0.4 ml of thionyl chloride in 1 ml of dimethyl formamide is added to the solution of 0.20 g (0.23 mmole) of 11'-nitrovincristine in 3 ml of dimethyl formamide under cooling with ice. The mixture is allowed to stand at 0° C. for 20 minutes and then at room temperature for additional 2 hours. Thereupon, the mixture is poured into 30 ml of ice-water, alkalized to pH 9 by adding concentrated ammonium hydroxide solution and extracted 3 times with 10 ml of ethyl acetate each containing 10% of ether. The combined organic phase is washed with saturated sodium chloride solution, dried over anhydrous magnesium sulphate and evaporated. The thus-obtained oily product is rubbed with 4 ml of ether, the formed yellow substance is filtered by suction and purified by using preparative TLC (at this point the product weighs 0.14 g) on a KG-PF$_{254+366}$ sheet by means of a developing system containing dichloromethane and methanol in a ratio of 20:2. The R$_f$ value of 15',20'-anhydro-11'-nitrovincristine is lower than that of the starting 11'-nitrovincristine. The elution is carried out with a 20:4 mixture of dichloromethane and methanol.

The aimed product is obtained in a yield of 60 mg (30%); m.p.: 220° C. (with decomposition) after recrystallization from methanol; $[α]_{546}^{22}$=+133.3° (c=0.36, chloroform).

IR (KBr, cm$^{-1}$): 3400 (OH), 1740 (ester CO), 1670 (NCHO).

MS 851 (M+, $C_{46}H_{53}N_5O_{11}$).

Method (b)

A solution containing 0.06 ml (0.09 g, 1.44 mmoles) of fuming nitric acid in 0.28 ml of glacial acetic acid is dropped to a solution containing 0.40 g (0.49 mmole) of 15',20'-anhydrovincristine in a solvent mixture containing 0.93 ml of glacial acetic acid and 1.2 ml of abs. chloroform at −20° C. under stirring. Thereupon, the stirring is continued at the same temperature for additional 3 hours, then the mixture is poured into 20 ml of ice-water, alkalized to pH 9 by adding concentrated ammonium hydroxide solution and extracted 3 times with 6 ml of dichloromethane each. The organic phases are combined, dried over anhydrous magnesium sulphate, then filtered and evaporated under reduced pressure. The thus-obtained residue weighing 0.45 g is purified by using preparative TLC on a KG-PF$_{254+366}$ sheet by means of a developing system containing dichloromethane and methanol in a ratio of 20:2. The elution is carried out with a 20:4 mixture of dichloromethane and methanol to give a yield of 70 mg (16%) of the aimed product, the physical and chemical characteristics of which are in complete agreement with those of the product obtained by the above method (a).

EXAMPLE 5

Preparation of 11'-nitrovincristine sulphate

The pH value of a solution containing 0.60 g (0.69 mmole) of 11'-nitrovincristine base in 3 ml of ethanol is adjusted to 5 by adding an ethanolic solution containing 2% of concentrated sulphuric acid under cooling with ice. The thus-formed sulphate salt is precipitated by adding 25 ml of ether, filtered by suction and washed with ether to give 0.61 g (91%) of the aimed sulphate salt.

We claim:

1. A nitro derivative of the formula (I),

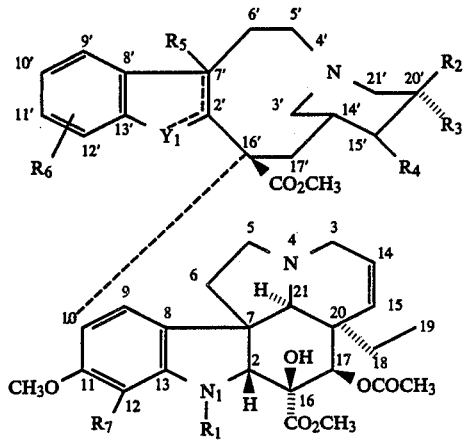

wherein
- $R_1$ is a methyl or a formyl group;
- $R_2$ is a hydroxy or ethyl group of $\beta$-position;
- $R_3$ is an ethyl group of $\alpha$-position;
- $R_4$ is a hydrogen atom; or
- $R_3$ and $R_4$ together is an oxygen bridge or a double bond;
- $R_5'$, $R_6$ and $R_7$ are nitro groups or hydrogen atoms with the proviso that simultaneously only one of $R_5$, $R_6$ and $R_7$ is a hydrogen atom; and
- Y is —N= when $R_5$ is a nitro grop; whereas
- Y is —NH— when $R_5$ is a hydrogen atom and a valence bond exists between the $C_2'$ and $C_7'$ atoms, as well as their pharmaceutically acceptable acid addition salts.

2. A compound selected from the group consisting of
12-nitrovinblastine,
11'-nitrovincristine,
9'-nitrovincristine,
7'-nitrovincristine,
N-formyl-11'-nitroleurosine,
N-formyl-7'-nitroleurosine,
15',20'-anhydro-11'-nitrovincristine,
as well as the pharmaceutically acceptable acid addition salts of these compounds.

3. A pharmaceutical composition having a cytostatic effect which comprises: a nitro derivative of the formula (I) as the active ingredient, wherein $R_1'$, $R_2'$, $R_3'$, $R_4'$ $R_5'$, $R_6$, $R_7$ and Y are as defined in claim 1, or a pharmaceutically acceptable acid addition salt thereof in admixture with a pharmaceutically acceptable carrier and/or additive.

* * * * *

UNITED STATES PATENT AND TRADEMARK OFFICE
CERTIFICATE OF CORRECTION

PATENT NO. : 4,746,665

DATED : May 24, 1988

INVENTOR(S) : Szantay et al.

It is certified that error appears in the above-identified patent and that said Letters Patent is hereby corrected as shown below:

In the Abstract

Add bond between "$R_3$" and "20'".

"16" should be connected with "10".

In the Specification:

Column 8, line 11, delete "grop" and insert --group--.

Signed and Sealed this

Eleventh Day of October, 1988

Attest:

DONALD J. QUIGG

Attesting Officer

Commissioner of Patents and Trademarks